US012678601B2

(12) United States Patent (10) Patent No.: US 12,678,601 B2
Shilo et al. (45) Date of Patent: Jul. 14, 2026

(54) URETERAL STENTS AND METHODS FOR USING THE SAME

(71) Applicants: Mor Research Applications Ltd., Ramat Gan (IL); Yeda Research and Development Co. Ltd., Rehovot (IL)

(72) Inventors: Yaniv Shilo, Ramat Gan (IL); Brian Berkowitz, Rehovot, IL (US)

(73) Assignees: Mor Research Applications Ltd., Ramat Gan (IL); Yeda Research and Development Co. Ltd., Rehovot (IL)

( * ) Notice: Subject to any disclaimer, the term of this patent is extended or adjusted under 35 U.S.C. 154(b) by 824 days.

(21) Appl. No.: 17/906,243

(22) PCT Filed: Mar. 18, 2021

(86) PCT No.: PCT/IB2021/052274
§ 371 (c)(1),
(2) Date: Sep. 13, 2022

(87) PCT Pub. No.: WO2021/186384
PCT Pub. Date: Sep. 23, 2021

(65) Prior Publication Data
US 2023/0125981 A1 Apr. 27, 2023

(30) Foreign Application Priority Data
Mar. 19, 2020 (IL) .......................................... 273468

(51) Int. Cl.
*A61M 27/00* (2006.01)
*A61F 2/04* (2013.01)
(Continued)

(52) U.S. Cl.
CPC ............. *A61M 27/008* (2013.01); *A61F 2/04* (2013.01); *A61F 2002/048* (2013.01); *A61M 25/0068* (2013.01); *A61M 25/04* (2013.01)

(58) Field of Classification Search
CPC ..... A61F 2/04; A61F 2002/048; A61M 25/04; A61M 25/0068; A61M 27/008
See application file for complete search history.

(56) References Cited

U.S. PATENT DOCUMENTS 4,610,657 A 9/1986 Densow
4,813,925 A * 3/1989 Anderson, Jr. ........... A61F 2/88
604/93.01
(Continued)

FOREIGN PATENT DOCUMENTS

EP 3517162 A1 7/2019
WO 2014116718 A1 7/2014
(Continued)

OTHER PUBLICATIONS

International Search Report and Written Opinion of International Searching Authority for PCT/IB2021/052274, European Patent Office (EPO), ISA/EP, Rijswijk, Netherlands, Dated: Aug. 6, 2021.
(Continued)

*Primary Examiner* — Rebecca E Eisenberg
*Assistant Examiner* — Timothy L Flynn
(74) *Attorney, Agent, or Firm* — M&B IP Analysts, LLC

(57) ABSTRACT
Embodiments pertain to ureteral stents for treatment of partial or full ureteral occlusion by bridging one or more ureteral occlusions, where each stent includes a tubular portion, a first spout portion and a second spout portion. The stent may have one or more tapered edges by having the smallest diameter of the first and/or the second spout portion smaller than the largest diameter of the tubular portion, and/or be of an overall length allowing the ureteral stent to be completely located within a patient's ureter once deployed therein.

20 Claims, 9 Drawing Sheets

(51) Int. Cl.
    *A61M 25/00*        (2006.01)
    *A61M 25/04*        (2006.01)

(56)               References Cited

U.S. PATENT DOCUMENTS

| | | |
|---|---|---|
| 7,883,516 B2 | 2/2011 | Huang et al. |
| 2010/0114292 A1* | 5/2010 | Heaton .................. A61F 2/064 |
| | | 623/1.36 |
| 2010/0145467 A1 | 6/2010 | Davoudi et al. |
| 2010/0274231 A1 | 10/2010 | Pravong et al. |
| 2013/0267990 A1 | 10/2013 | Behl et al. |
| 2016/0001050 A1 | 1/2016 | Yee et al. |
| 2017/0095651 A1 | 4/2017 | Hutchins, III et al. |
| 2017/0202688 A1* | 7/2017 | Caldwell ............. A61M 27/008 |

FOREIGN PATENT DOCUMENTS

| WO | 2017120332 A1 | 7/2017 |
|---|---|---|
| WO | 2018200060 A1 | 11/2018 |

OTHER PUBLICATIONS

International Search Report and Written Opinion of International Searching Authority for PCT/IB2021/052274, European Patent Office (EPO), ISA/EP, Rijswijk, Netherlands, Dated: Aug. 18, 2021.
Israel Office Action and search report mailed Jul. 1, 2020 for Patent Application No. 273468 dated Jan. 7, 2020, 21 pages.

\* cited by examiner

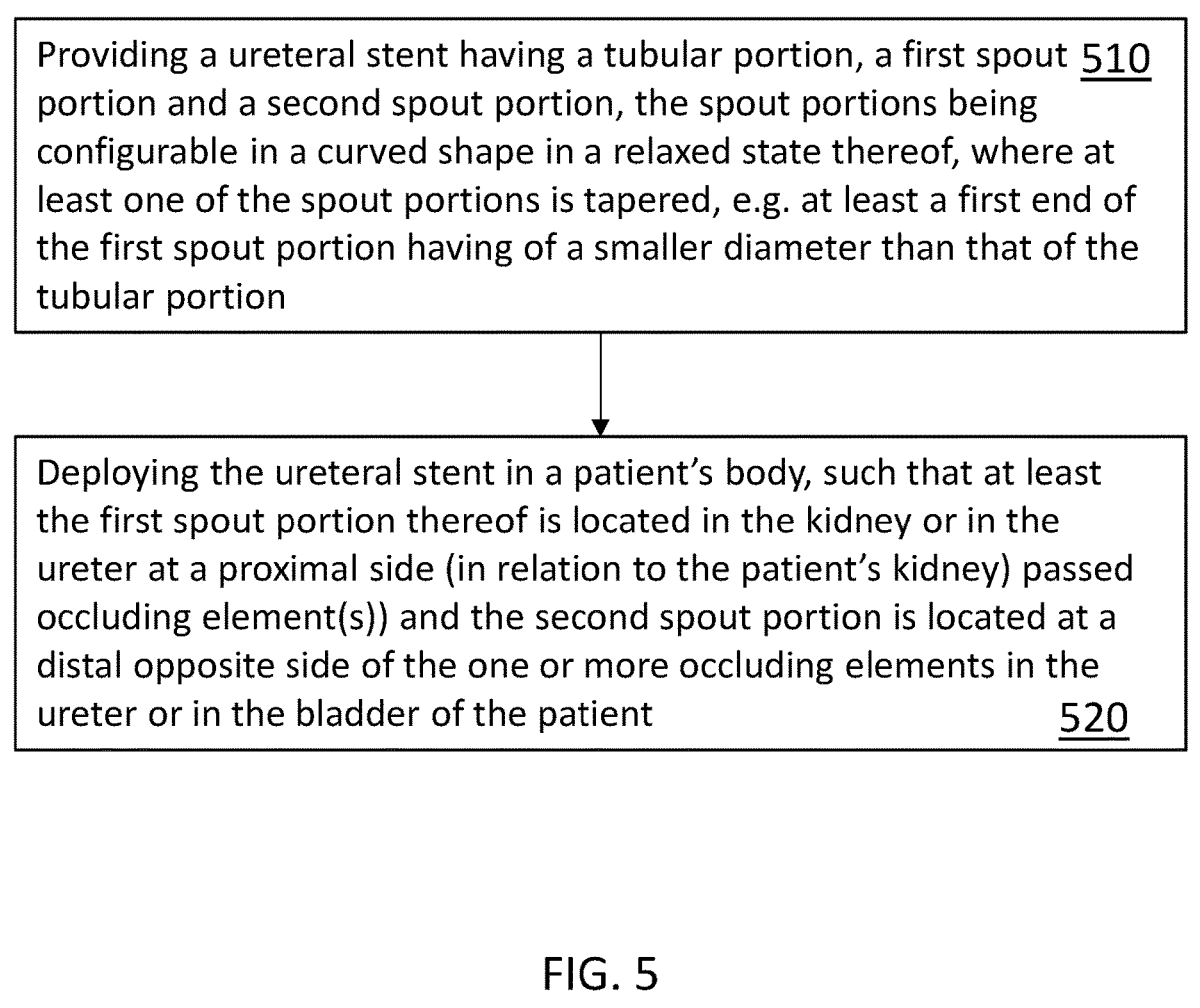

Providing a ureteral stent having a tubular portion, a first spout 510
portion and a second spout portion, the spout portions being
configurable in a curved shape in a relaxed state thereof, where at
least one of the spout portions is tapered, e.g. at least a first end of
the first spout portion having of a smaller diameter than that of the
tubular portion Deploying the ureteral stent in a patient's body, such that at least
the first spout portion thereof is located in the kidney or in the
ureter at a proximal side (in relation to the patient's kidney) passed
occluding element(s)) and the second spout portion is located at a
distal opposite side of the one or more occluding elements in the
ureter or in the bladder of the patient                     520

FIG. 5

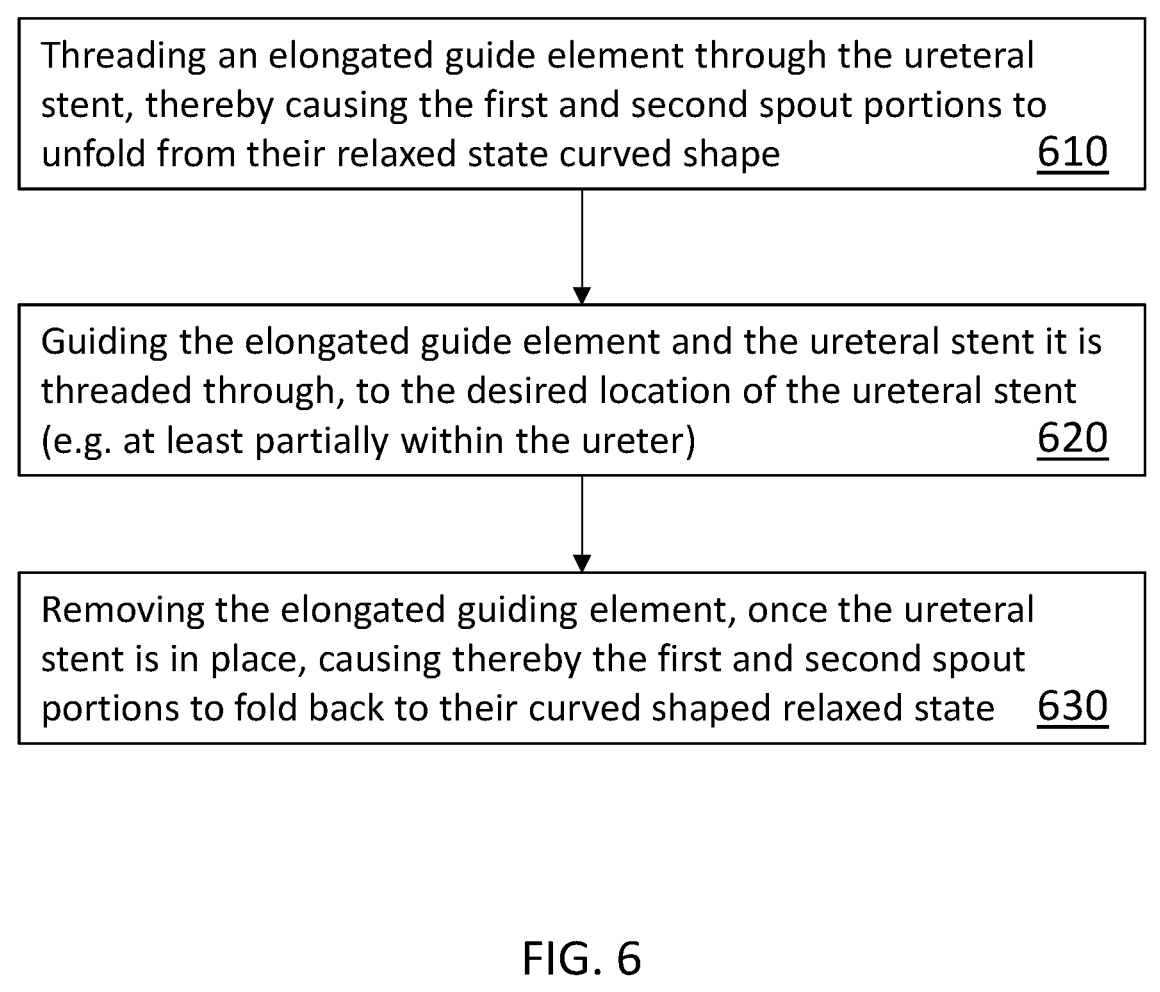

Threading an elongated guide element through the ureteral stent, thereby causing the first and second spout portions to unfold from their relaxed state curved shape          610

Guiding the elongated guide element and the ureteral stent it is threaded through, to the desired location of the ureteral stent (e.g. at least partially within the ureter)          620

Removing the elongated guiding element, once the ureteral stent is in place, causing thereby the first and second spout portions to fold back to their curved shaped relaxed state     630

FIG. 6

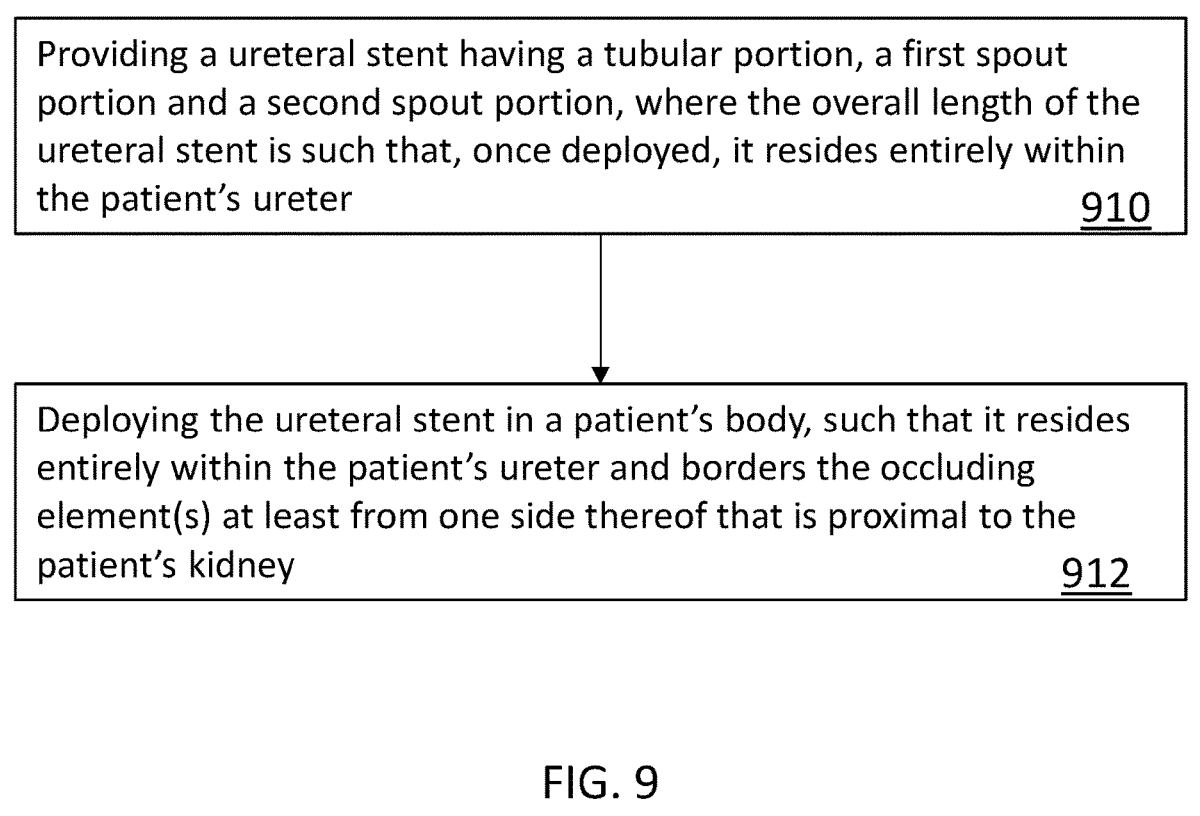

Providing a ureteral stent having a tubular portion, a first spout portion and a second spout portion, where the overall length of the ureteral stent is such that, once deployed, it resides entirely within the patient's ureter     910

Deploying the ureteral stent in a patient's body, such that it resides entirely within the patient's ureter and borders the occluding element(s) at least from one side thereof that is proximal to the patient's kidney     912

FIG. 9

URETERAL STENTS AND METHODS FOR USING THE SAME

The present disclosure relates in general to ureteral stents, catheters, and systems and method for using thereof for treatments of ureteral occlusions such as ureteral stones.

BACKGROUND

Ureteral and renal calculi may cause ureteral stones (also called kidney stones) causing various medical hazards and pain to the patient. Large sized ureteral stones or clusters of several stones may engage the inner wall of the ureter and cause severe pain, occlude the ureter or even damage the inner ureter tissue.

Small sized ureteral stones are often treated by prescribing the patient with pain medication, if necessary, and instructing him/her to intake large amounts of fluids per day, with the aim of facilitating or encouraging natural excretion of the ureteral stones. In some cases, non-intrusive treatment is given to reduce the size of the stones, by using for example designated medications, for dissolving or corroding the stones, ultrasound-based therapy such as lithotripsy, which causes fragmentation of the ureteral stones by exertion of ultrasonic shock waves, etc. In cases in which the ureteral stones are too large and/or cause severe irritation or pain, and/or in cases in which non-intrusive treatment(s) fail, intrusive treatment may be required such as surgical removal of the ureteral stones.

BRIEF DESCRIPTION OF THE FIGURES

The figures illustrate generally, by way of example, but not by way of limitation, various embodiments discussed in the present document.

For simplicity and clarity of illustration, elements shown in the figures have not necessarily been drawn to scale. For example, the dimensions of some of the elements may be exaggerated relative to other elements for clarity of presentation. Furthermore, reference numerals may be repeated among the figures to indicate corresponding or analogous elements. References to previously presented elements are implied without necessarily further citing the drawing or description in which they appear. The figures are listed below.

FIG. 5 shows a flowchart of a process or method for prevention of ureter occlusion, using a ureteral stent having at least one tapered edge, according to some embodiments;

FIG. 6 shows a flowchart of a process or method for deployment of a ureteral stent having at least one tapered edge, according to some embodiments;

FIG. 9 shows a flowchart of a process for prevention of ureter occlusion, using a short ureteral stent, according to some embodiments.

DETAILED DESCRIPTION

Figure 1A:
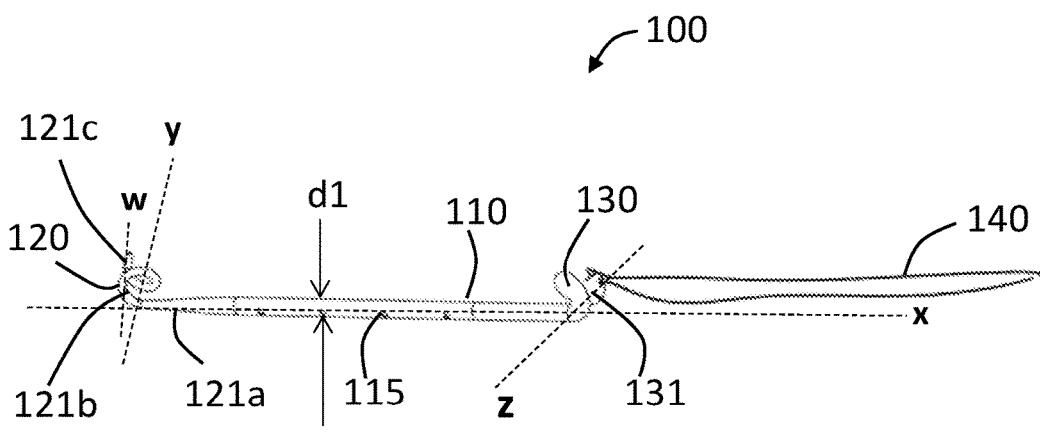
FIG. 1A shows a first view of a tapered ureteral stent having a pigtail tapered edge, according to some embodiments.

Aspects of embodiments pertain to ureteral stents that can be used for presurgical treatment of ureteral occlusion and may be configured for bypassing the occlusion(s) in the ureter and thereby allow fluid passage from the kidney to the bladder, e.g., to prevent pressure from building in the patient's kidney and/or complete blockage of the ureter and kidney. Although embodiments may pertain to bypassing an occlusion in the ureter, this should by no means be construed in a limiting manner. Accordingly, devices and methods may pertain to a variety of additional or alternative applications including, for example, ureteral strictures from any cause, or external ureteral obstruction due to benign and malignant lesions. In addition, the device can be used for post-operative drainage of the ureter after endourological procedures such as ureteroscopy or percutaneous nephrolithotomy, as well as ureter wound healing (due to, e.g., surgeries, injuries, etc.), incontinence treatment, and/or the like.

A ureteral stent may be configured as a thin tube (e.g., cannula, tubule, etc.) that can be inserted at least partially into the ureter through the patient's urethra and bladder, e.g., by using a guide wire, inserted through the tubular stent and then removed once the ureteral stent is fully deployed in a desired location and/or position.

It is noted that the term "bladder" refers to the "urinary bladder" and may be used herein interchangeably.

It is noted that the term "occlusion" or "occluding element" used herein may refer to any obstacle, element, stone, a cluster of stones, sediment(s), tumor, cyst, or any other object that obstructs, occludes and/or causes any type of medical and/or physical discomfort and/or hazard.

Aspects of disclosed embodiments pertain to ureteral stents and systems, devices and/or methods for using thereof.

According to some embodiments, there is provided a ureteral stent that may include: a (straight) main tubular portion configured for fluid flow therethrough; a first spout portion, which extends from one end of the tubular portion, the first spout portion being configurable to a curved or spiral shape, in a relaxed state of the ureteral stent; and a second spout portion, which extends from another end of the tubular portion. In some examples, the first spout portion may serve as a proximal stent anchor and have in a deployed state, for example, a curved (e.g., a spiral) shape. In some examples, the second spout portion may serve as a distal stent anchor and have in a deployed state, for example, a curved (e.g., a spiral) shape. Optionally, the spout portions may be tubular. In some examples, the spout portions as well as the main tubular portion may have openings to allow the flow of fluid into the stent's tubular cavity (from the side of the kidney), and further to allow outflow or drainage of fluid from the stent's tubular cavity toward the bladder to bypass an occluding element.

In some embodiments, at least a portion of the stent's tubular cavity may be sealed to facilitate, for example, bypassing a surgical site of the ureter (e.g., an anastomosis site).

In the discussion that follows, the first spout portion may be considered positioned "proximal" to the kidney and the second spout portion may be considered positioned "distal" to the kidney, during stent deployment and when set in an operable configuration within the patient body.

According to some embodiments, the first and/or the second spout portions may protrude from the diameter of the tubular portion such as to bracket the one or more occluding elements bordering the occluding element(s) at least from one side thereof that is proximal to the patient's kidney, for preventing the occluding element(s) from reaching the kidney. To bracket the one or more fully or partially occluding element(s), the first and second spout portions may be configured to engage with the inner walls of the patient's ureter and/or with the one or more occluding elements.

According to some embodiments, the first spout portion and/or the second spout portion may be at least partially spirally shaped defining a first and/or a second spiral axis, respectively.

In some examples, the diameter of at least part of the first spout portion and/or the second spout portion may be smaller than the diameter of at least part of the tubular portion. For example, a tip or at least a part of one or more of the spout portions, may be tapered towards their respective stent ends. A (fully or partially) tapered or narrowing configuration of the proximal spout portion may for instance allow easier insertion into and passage of the stent through the urethra, past the bladder and further into the ureter. A tapered or narrowing configuration may also facilitate pushing the proximal stent portion and, optionally, a portion of the main stent portion past a (fully or partially) occluded section of the ureter. A section of the ureter may be occluded due to one or more of the following: an occluding element (e.g., stone), a stricture, and/or a narrowed and/or occluded ureter portion. For example, a stent portion proximal to the kidney may be tapered towards and terminate at the stent's proximal end to facilitate deployment (e.g., pushing) of at least the proximal end portion of the stent past a kidney stone.

The proximal tapered stent portion may have a length of, for example, at least 1 cm, at least 2 cm, at least 3 cm, at least 4 cm, or at least 5 cm, along a longitudinal axis of the stent. The length measurement may pertain to a configuration where the stent is in a strained state.

In some embodiments, the proximal tapered portion may begin where the stent's curved portion, proximal to the kidney, terminates, and extend from there to the stent's proximal end. Correspondingly, the stents curved may not be tapered.

In some embodiments, the length of the proximal tapered stent portion may include at least a portion of the stent portion that is configured to assume, in a relaxed state, a curved configuration. Accordingly, in some examples, at least some or the entire curved portion may be tapered towards the proximal end.

It is noted that the tapered configuration may be applicable to any kind of stent ureteral stent configuration. For example, a proximal stent portion may be tapered towards the proximal end, regardless of the length of the stent and/or an orientation of the axis around which the curved portion is twisted in relation to a main stent axis and/or the number of full spiral turns or convolutions of the proximal and/or distal spout portion. The ureteral stent may be configured to be at least partially deployed in a patient's ureter such that the first spout portion is located in the patient's kidney or in the ureter, at a smaller distance from the patient's kidney than the second spout portion, to enable, when deployed in the patient's body, fluid passage between the kidney and the bladder of the patient, by bypassing one or more partially and/or fully occluding elements located in the patient's ureter.

The inner diameter of the tubular portion, or the diameter over at least a main length thereof, may be significantly larger than the diameter of the edge of at least the first spout portion, to be thick enough to allow easy fluid passage therethrough, while bridging over the occluding element(s) in the ureter.

For example, the widest diameter of the tubular portion may range between 4.8 F and 8 F (approximately between 1.6 mm and 2.67 mm), while the narrowest diameter of the first and/or second spout portion may range between 3.6 F and 6 F (approximately between 1.2 mm and 2 mm). The ratio between the widest diameter of the tube portion and the narrowest diameter of the first and/or second spout portions may range, for instance between 1.33 and 2.22.

According to some embodiments, the tubular portion of the ureteral stent may be porous having one or more openings to allow fluid flow therethrough.

According to some embodiments, the average length of the tubular portion of the ureteral stent may be equal to or smaller than the average length of an adult patient's ureter, which may range between 24 cm and 28 cm.

According to some embodiments, the overall length of the ureteral stent may be, such that once deployed in a patient's body, the first spout portion of the ureteral stent is positioned in the patient's ureter or kidney and the second spout portion of the ureteral stent is located in the patient's bladder.

According to some embodiments, the overall length of the ureteral stent may be such that once deployed in a patient's body, the first spout portion of the ureteral stent is positioned in the patient's ureter or kidney and the second spout portion of the ureteral stent is positioned in the patient's ureter and not in the bladder.

According to these embodiments, the overall length of the ureteral stent may be smaller than the overall length of the ureter of the specific patient requiring deployment of the respective ureteral stent. For example, the overall length of the ureteral stent may be such that once deployed in a patient's body, both the first and the second spout portions of the ureteral stent, in the relaxed state, are positioned in the patient's ureter. Otherwise stated, the stent, when operably deployed and in the relaxed state, resides entirely within the ureter. In such configuration, no curved and/or other stent portion extends into the kidney (or into or beyond the ureteropelvic junction) and bladder (or into or beyond the ureterovesical junction).

Accordingly, in some embodiments, there is provided a ureteral stent for the prevention of ureter occlusion that may include: a tubular portion having an elongated hollow tubular shape having a first end and a second end, the tubular portion being configured for enabling fluid flow therethrough; a first spout portion, which extends from the first end of the tubular portion, and configurable to a curved shape, in a relaxed state of the ureteral stent; and a second spout portion, which extends from the second end of the tubular portion, the second spout portion being configurable to a curved shape, in a relaxed state of the ureteral stent, where the overall length of the ureteral stent, at least in a relaxed state thereof, is such as to be completely located within a patient's ureter once deployed therein.

The overall length of a stent configured to reside entirely within the ureter, in the relaxed state may be, for example, up to 4 cm, up to 6 cm, 7 cm, 8 cm, 9 cm, 10 cm, 11 cm, 12 cm, 13 cm, 14 cm, 15 cm, 16 cm, 17 cm, 18 cm 19 cm, 20 cm, 21 cm, 22 cm, 23 cm, 24 cm, 25, 26 cm, 27 cm, or 28 cm.

Stents which are configured to completely reside within the patient's ureter may, for example, reduce the likelihood of or eliminate the occurrence of pain and/or irritation, which might otherwise occur if stent portions were to reside within the kidney and/or the bladder.

In some embodiments, the stent may include a proximal and distal anchor. The proximal and the distal anchor may both be configured to engage with (e.g., bracket) a stone located within the ureter. In some embodiments, to enable bracketing of one or more fully or partially occluding elements, at least from one side of the occluding element(s) that is proximal to the kidney, the first spout portion may be spirally curved defining a first spiral axis that is angular to the main axis; and/or the second spout portion is spirally curved defining a second spiral axis that is angular to the main axis.

Optionally, the overall length of the stent may be comparatively short to allow movement of the stent together with the stone along the ureter, until both the stone and the stent, in their entirety, are expelled into the bladder, e.g., due to gravitation and/or peristaltic ureter activity. The stent may be configured such that during movement of the stent together with the stone along the ureter, fluid communication between the kidney and bladder is maintained.

As mentioned herein, a stent anchor may for example have a curved shape. In some examples, a (stent) anchor may have a spiral shape delineating, for example, at least one or a plurality of complete convolutions.

Optionally, a proximal anchor may have a generally curved shape, and a distal anchor may have a spiral shape. Optionally, a proximal anchor may have a generally spiral shape, and a distal anchor may have a curved shape. Optionally, both the proximal and the distal anchor may have a curved shape. Optionally, both the proximal and the distal anchor may be formed as spirals.

In some embodiments, a proximal and distal anchor may each include a spiral having the same number of convolutions. In some embodiments, the number of convolutions of a spiral of a proximal anchor may differ from the number of convolutions of a spiral of a distal anchor.

In some embodiments, the spirals of the proximal anchor may have convolutions of increasing diameter towards the proximal end.

In some embodiments, the spirals of the proximal anchor may have convolutions of decreasing diameter towards the proximal end.

In some embodiments, the spirals of the distal anchor may have convolutions of increasing diameter towards the distal end.

In some embodiments, the spirals of the distal anchor may have convolutions of decreasing diameter towards the distal end.

In some embodiments, the spirals of the proximal anchor may have convolutions of decreasing diameter, followed by convolutions of increasing diameter towards the proximal end.

In some embodiments, the spirals of the proximal anchor may have convolutions of increasing (Incr) diameter, followed by convolutions of decreasing (Decr) diameter towards the proximal end.

Optionally, anchors may have increasing Incr-Decr-Incr or Decr-Incr-Decr spiral configurations. Optionally, anchors may have Incr-Decr-Incr or Decr-Incr-Decr spiral configurations. Additional or alternative spiral configurations may be conceived.

In some embodiments, the distal and proximal end portions may terminate in a curved manner. For example, curved or spiral anchor tips may constitute the stent ends.

In some embodiments, the proximal and/or distal anchor may terminate in a corresponding proximal and/or distal straight stent portions which terminate in corresponding stent tips or ends.

The proximal and/or distal straight stent portions may be (substantially) in alignment with or (substantially) parallel to the stent's main axis. In some other examples, the proximal and/or the distal anchor may terminate in a respective proximal and/or distal straight stent portion that forms an angle relative to the stent's main axis. Accordingly, in some examples, a tip of the first spout portion and/or of the second spout portion may be directed inwardly, outwardly or in parallel to a main axis of the tubular portion.

In some embodiments, a stent may be dumbbell shaped. The wide portions may constitute anchors (e.g., in the form of spirals) and may, optionally, be configured to simultaneously engage, for example, a ureter occluding element such as a stone. In some examples, the overall length of such stent may range for example, from 4 cm to about 28 cm, yet the stent may be still short enough to completely reside within the ureter. The narrow portion between the two anchors may have a length allowing the two anchors to simultaneously engage with an occluding element.

In some embodiments, the stent design may be personalized, for example, according to the patient's ureter length and/or dimensions of the occluding element.

For example, the usual length of an adult patient's ureter is approximately 24 cm to 28 cm, so that the maximal length of the ureteral stent may be shorter than 24 cm to 28 cm. In some examples, a kit may be provided including a plurality of stents each having different (e.g., lengths and/or anchor) configuration. A stent selection may be made based on the patient's ureter length (which may for instance be determined or measured via imaging and/or estimated based on the patient's height, age, gender, etc.) and/or based on the size and/or location of the one or more fully or partially occluding elements in the patient's ureter and/or any other clinical condition.

Some embodiments pertain to personalized manufacturing (e.g., 3D or additive printing) of a stent, specifically configured to a patient's urinary tract and/or location and/or size of the patient's clinical condition as determined, for example, through the employment of one or more imaging techniques.

According to some embodiments, the first spout portion and/or the second spout portion curved shape may be such that its overall width is larger than the diameter and/or width of the tubular portion, e.g. having dimensions of roughly the inner wall diameter of the ureter, in order to border the one or more fully or partially occluding element(s) for preventing the one or more occluding elements from moving at least towards the kidney and/or for enclosing (bordering) the one or more occluding elements within an area bracketed by the stent for preventing the one or more occluding elements from escaping the stent enclosed area.

In some cases, there is a need for the occluding element(s) to be bordered only in the direction leading to the kidney connected to the specific ureter, to allow the occluding element(s) to move towards the bladder for it(them) to be naturally excreted. In such cases, only the first spout portion, closer to the kidney or located in the kidney, may be of bracketing dimensions (e.g., of overall width close to the diameter of the ureter's inner wall), while the second spout portion may be smaller in overall size and dimensions.

In other cases, requiring maintaining the one or more occluding element(s) inside the ureter until surgical removal thereof, both first and second spout portions may be of overall size and dimensions that bracket the one or more occluding element(s) from both sides thereof.

According to some embodiments, the curved shape of the first spout portion and/or of the second spout portion may be in the form of a spiral shape, a pig tail shape, a conical spiral shape, a tapering spiral shape and/or any other shape that curves in respect to a main axis, defined by the tubular portion, when in a straight (e.g., stretched) state. For example, a tip of the first spout portion may be configured to be directed inwardly, outwardly or in parallel to the main axis of the tubular portion; and/or a tip of the second spout portion may be configured to be directed inwardly, outwardly or in parallel to the main axis of the tubular portion.

The tubular portion, the first spout portion and the second spout portion may all be configured as a single integral stent piece made from the same material or made from a different material and/or removably or non-removably connectable to one another.

According to some embodiments, the first spout portion and/or the second spout portion may be configured to be transitioned from its/their relaxed state curved shape into a tensioned state when an elongated guide element is inserted through the ureteral stent (e.g. for guiding the ureteral stent through the patient's urethra for deployment thereof at least partially in the patient's ureter), where the first spout portion and/or the second spout portion are configured to reverse into the curved shape relaxed state when the elongated guide element is removed from the ureteral stent (e.g. once the deployment is completed).

The tubular portion, the first spout portion, and/or the second spout portion may be made from one or more shape memory and/or elastic/flexible materials (such as smart material(s) enabling reverting to a preconditioned shape or a shape similar thereto when no tension or force is applied or exerted).

According to some embodiments, to achieve a ureteral stent having one or more tapered edges (spout portions), in which the diameter of its edges is smaller than the diameter of its middle section (tubular portion), one or more ends of the tubular portion may have a tapered edge.

In one example, the ureteral stent may be made from a single tubular piece having curved tapering edges, forming the first and second spout portions.

According to some embodiments the diameter of the edge (tip) of the first spout portion may be smaller than the diameter of the tubular portion as well as from the diameter of the second spout portion.

According to some embodiments, the tubular portion may have an hourglass shape, for gradual narrowing and subsequent widening of the diameter of the tubular portion from the first spout tip towards the second end.

According to some embodiments, the ureteral stent may also include a string connected to the second (distal) end of the tubular portion or to the second (distal) spout portion, e.g., for easy and convenient removal of the ureteral stent. In some examples, the string may be configured so that it can distally extend into the bladder (e.g., but not further). In some examples, the string may be configured so that it can extend through the bladder into the urethra (e.g., but not further). In some further examples, the string may be configured so that it can distally extend through the bladder and into the urethra to outside the body. It is noted that the term "string" as used herein may also encompass, for example, threads, strands, filaments, wires, twines, twists, yaw strings and/or the like.

The ureteral stent may be made from one or more elastic materials enabling to curve and bend at least during deployment of the ureteral stent in the patient's body and optionally also in response to peristalsis and/or other movements of the ureter.

According to some embodiments, the deployment of the ureteral stent in the patient's body may be carried out by threading an elongated guide element such as a guide wire through the ureteral stent, where the threading of the elongated guide element causes the first and/or second spout portions to unfold from their relaxed state curved shape (e.g. forming a single tube shape); guiding the elongated guide element and the ureteral stent it is threaded through, to the ureter of a patient such that the first spout portion bypasses the one or more partially or fully occluding elements in the ureter (e.g. such that the first spout portion reaches the kidney or a location in the ureter proximal to the kidney), the tubular portion is located over the one or more partially or fully occluding elements and the second spout portion is located at another side of the one or more partially or fully occluding elements opposite the location of the first spout portion; and then removing the elongated guiding element, once the ureteral stent is in the desired location and position, thereby causing the first and second spout portions to attain their relaxed state, for enclosing the one or more occluding elements at least from one side thereof that is proximal to or in the kidney.

According to some embodiments, the deployment of the ureteral stent may be carried out also by using one or more imaging systems (such as ultrasound, camera probe (endoscopic) and/or any other imaging devices or systems) for detecting the location of the ureteral stent throughout the deployment process.

FIG. 1A, FIG. 1B, FIG. 2A and FIG. 2B show various views of a ureteral stent 100 with one tapered edge, according to some embodiments. The ureteral stent 100 includes a tubular portion 110, which defines a main axis x, a first spout portion 120, which has a curved (e.g., pig tail or spiral) tapered shape, a second spout portion 130, which has a curved (e.g., pig tail or spiral) shape and a string 140 connectable to the second spout portion 130. The first and second spout portions 120 and 130 extend from opposite sides of the tubular portion 110.

According to some embodiments, the ureteral stent 100 may be configured to bypass one or more fully or partially occluding elements (herein also "element(s)" or "occluding element(s)") such as ureteral and/or kidney stone(s), once deployed at least partially in the ureter of a patient, by deploying the ureteral stent 100 such that the first spout portion 120 thereof is located at one side of the occluding element(s) that is proximal to the patient's kidney or in the patient's kidney, the tubular portion 110 is located over the occluding element(s) and the second spout portion 130 is located at another, opposite side of the occluding element(s), distal from the patient's kidney and proximal to the patient's bladder. In this way the ureteral stent 100 can fully bridge the occluding element(s) for enabling fluid flow between the kidney and the bladder of the patient.

According to some embodiments, the tubular portion 110 may be configured as a cylindrical tube, which may be porous, including multiple openings 115, for improving fluid flow therethrough. The largest diameter of the tubular portion 110 is defined by d1, as shown in FIG. 1A.

According to some embodiments all tubular parts of the ureteral stent 100, i.e., the tubular portion 110, the first spout portion 120 and the second spout portion 130 may be tubular having a hollow cavity through which fluid can flow, such that the spout portions 120 and 130 connect to the edges of the tubular portion (whether integrally or removably) and having proximal and distal openings 125 and 135 (see FIG. 2B), for allowing fluids flow therethrough.

According to some embodiments, the first spout portion 120 has a tapered base part 121a extending from one end of the tubular portion 110, a curved (e.g., spiraling) middle part 121b extended from the base part 121a and a tapered tip 121c. This configuration of the first spout portion 120 is such that the smallest diameter d2 of the first spout portion (see FIG. 2C) is significantly smaller than the widest diameter d1 of the tubular portion 110, e.g., by a factor (ratio) that ranges between 1.3 and 2.2. For example, if d1 is 4.8 F (approximately 1.6 mm) than the smallest diameter d2 of the first spout 120 (e.g., the diameter of the edge of its tip 121c) may be 3.6 F (approximately 1.2 mm).

The middle part 121b of the first spout portion 120 may be symmetrically curved (twisted) around an axis y, which may be angular to the main axis x, as shown in FIG. 1A.

According to some embodiments, the angle between x and y may not exceed 90 degrees.

According to some embodiments the minimum length of the smallest diameter of the first spout portion d2 may be limited by the size of the guide element (e.g., diameter of a guide wire) which is to be inserted therethrough for deployment of the ureteral stent 100. Typical diameter of guide wires used for ureteral stents deployment range between 0.8 mm and 1.1 mm, therefore the minimum threshold for the diameter of the first spout portion d2 when using such guide wires may be limited to 1.2 mm (3.6 F).

Figure 2A:
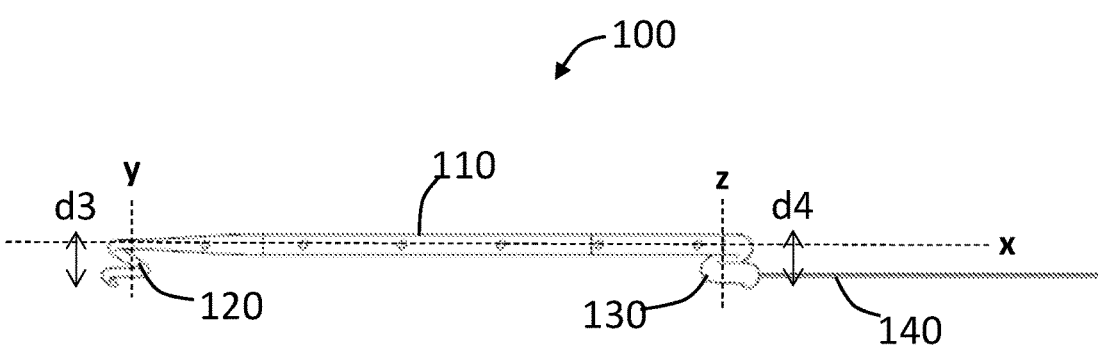
FIG. 2A shows a third view of the tapered ureteral stent, according to some embodiments.
Figure 2B:
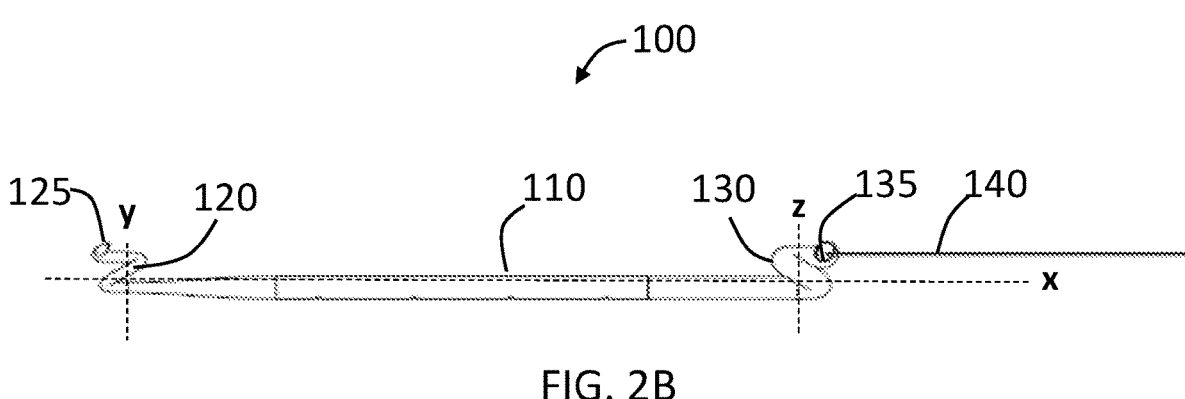
FIG. 2B shows a fourth view of the tapered ureteral stent, according to some embodiments.
Figure 2C:
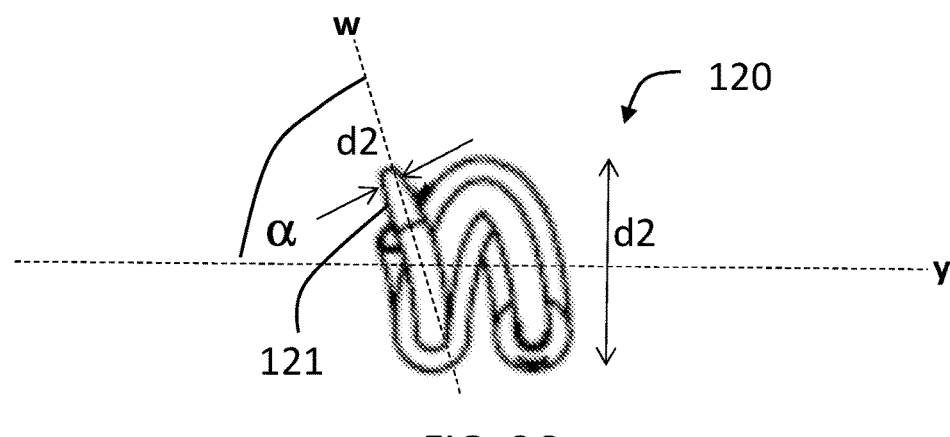
FIG. 2C shows the tapered edge of the tapered ureteral stent, according to some embodiments.

According to some embodiments, as shown in FIG. 1A and FIG. 2C, the tip 121c of the first spout portion 120 may be angular, in respect to the axis y about which the other spiraling part of the spout portion 120 is symmetrical. The direction of the tip 121c defined by axis w may form an acute angle α (alpha) with axis y.

According to some embodiments, the second spout portion 130 may be configured as a spiral shape, symmetrically spiraling about an axis z, which may be angular in respect to the main axis x (e.g., where the angle between axes x and z may not exceed 90 degrees).

Figure 1B:
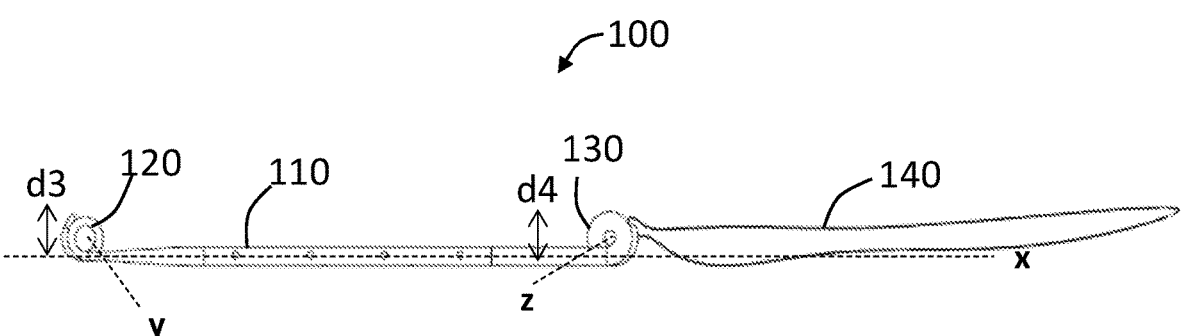
FIG. 1B shows a second view of the tapered ureteral stent, according to some embodiments.

According to some embodiments, as shown in FIGS. 1A-B to and 2A-2C, the angularity of the first and second spout portions 120 and 130, in respect to the main axis x, form a bordering structure, enabling to enclose therebetween the occluding element(s) once the ureteral stent 100 is deployed.

At least one of: the overall width of the first spout portion d3 and/or the overall width of the second spout portion d4 (see FIG. 1B and/or FIG. 2A) may be significantly larger than the largest width of the tubular portion d1, to prevent the occluding element(s) from drifting inside the patient's ureter at least towards the kidney and optionally, also from drifting towards the bladder. This may be achieved by having the first and the second spout portions 120 and 130 protrude from the border contours of the tubular portion 110, such that at least the second spout portion 130 engages with the inner walls of the ureter and/or the occluding element(s), and the first spout portion 120 is either located in the patient's kidney, once deployed or engages the inner wall of the patient's ureter and/or the occluding element(s).

In the embodiments illustrated in FIGS. 1A-B to and 2A-2C, the tip 131 of the second spout portion 130 is not tapered and has the same diameter d1 of the tubular portion 110 throughout the second spout portion 130. In other cases, the second spout portion may also be tapered.

Figure 3:
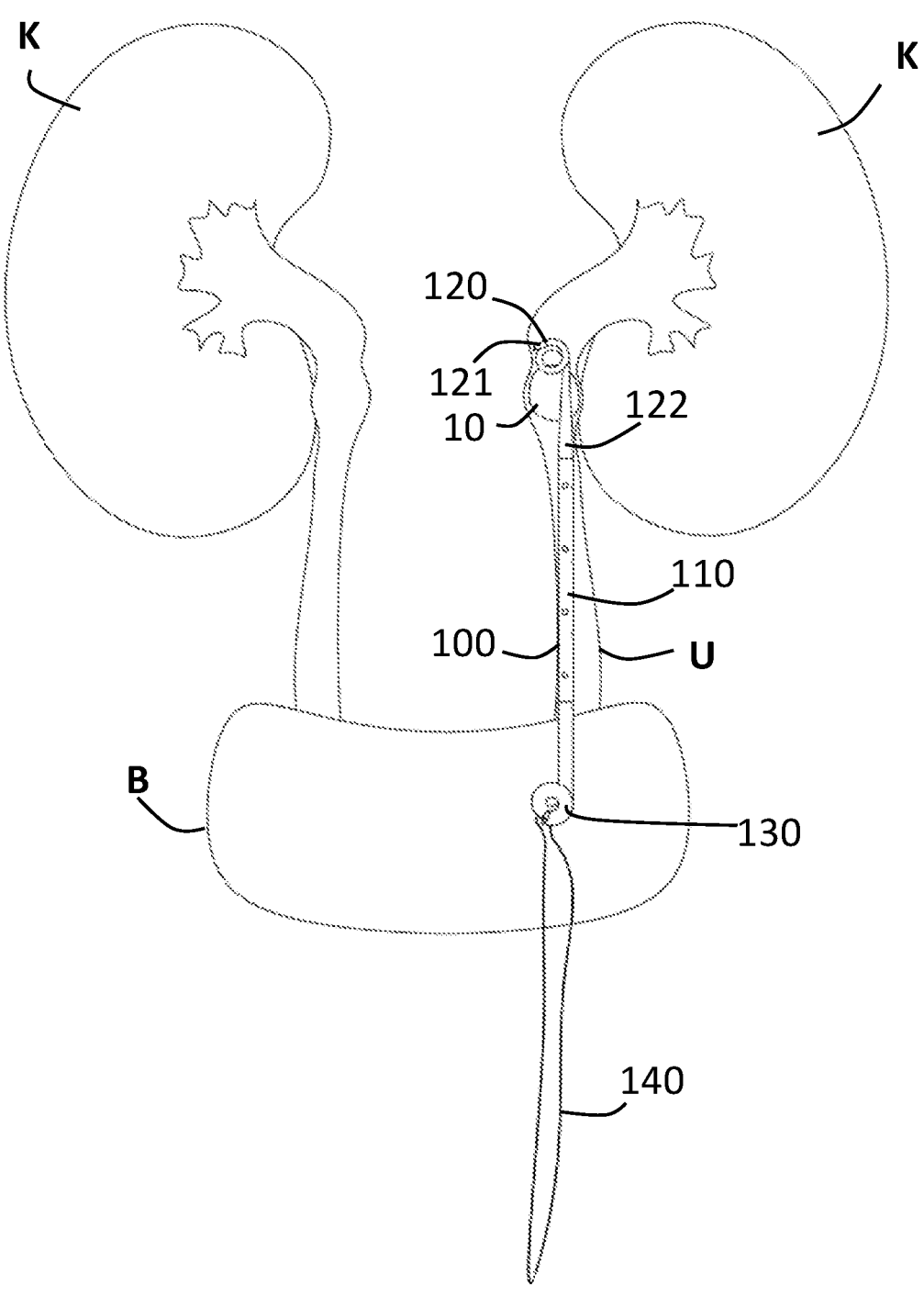
FIG. 3 shows the tapered ureteral stent deployed in a ureter of a patient, according to some embodiments.

FIG. 3 shows the ureteral stent 100, when deployed in a patient's body, according to some embodiments. In this case one ureter U of the patient has an occluding element 10 located at an upper side of the ureter U proximal to the kidney K. The ureteral stent 100 may be deployed partially in the ureter U such that the first spout portion 120 thereof is located at one side of the occluding element 10 that is proximal to the kidney K, and the second spout portion 130 is located in the patient's bladder B, where the tubular portion 110 is located over the occluding element 10 such as to form a bridging channel for allowing fluids to flow from the kidney K to the bladder B, preventing thereby complete or partial occlusion of the ureter U. Tubular portion 110 may have a tapered section 122 configured to taper proximally and extend into further tapering first spout portion 120.

Figure 4:
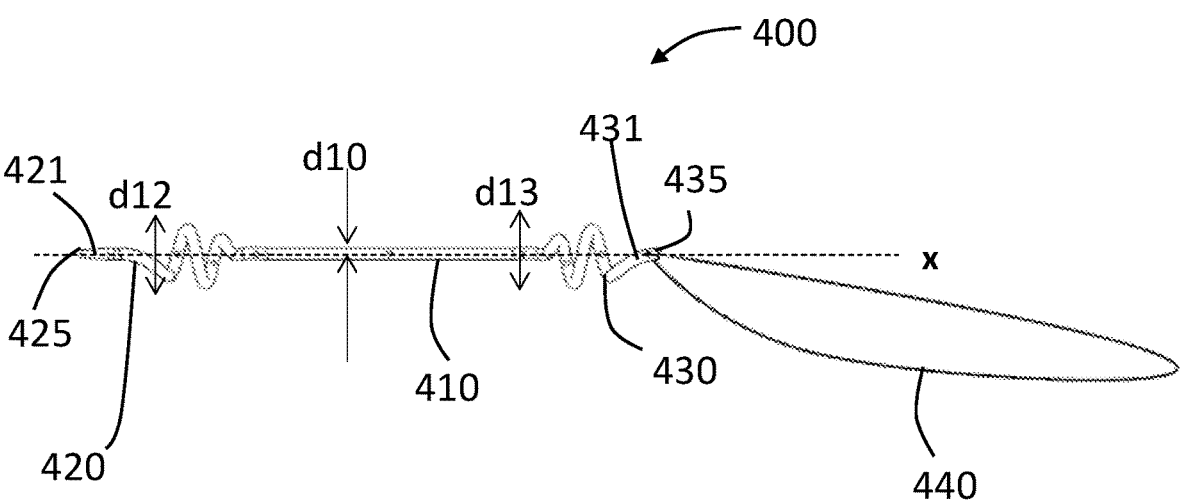
FIG. 4 shows a tapered ureteral stent having a spiral tapered edge, according to some embodiments.

FIG. 4 shows a ureteral stent 400 with at least one tapered edge, according to some embodiments. The ureteral stent 400 includes a tubular portion 410, which defines a main axis x, a first spout portion 420, which has a curved (e.g., spiral) tapered shape, a second spout portion 430, which has a curved (e.g., spiral) shape and a string 440 connectable to the second spout portion 430. The first and second spout portions 420 and 430 extend from opposite sides of the tubular portion 410.

According to some embodiments, the ureteral stent 400 may be configured to bypass one or more fully or partially occluding elements (herein also "element(s)" or occluding element(s)") such as ureteral and/or kidney stones, once deployed at least partially in the ureter of a patient, by deploying the ureteral stent 400 such that the first spout portion 420 thereof is located at one side of the occluding element(s) that is proximal to the patient's kidney or in the patient's kidney, the tubular portion 410 is located over the occluding element(s) and the second spout portion 430 is located at another, opposite side of the occluding element(s), distal from the patient's kidney and proximal to or inside the patient's bladder. In this way the ureteral stent 400 can fully bridge the occluding element(s) for enabling fluid flow between the kidney and the bladder of the patient.

According to some embodiments, the tubular portion 410 may be configured as a cylindrical tube, which may be porous, including multiple openings, for improving fluid flow therethrough. The largest diameter of the tubular portion 410 is defined by d10.

According to some embodiments, the tubular portion 410, the first spout portion 420 and the second spout portion 430 of the ureteral stent 400, may be tubular having a hollow cavity through which fluid can flow, such that the spout portions 420 and 430 connect to the edges of the tubular portion 410 (whether integrally or removably) and having openings 425 and 435, for allowing fluids flow therethrough.

According to some embodiments, the first and second spout portions 420 and 430 may be configured at least partially as a spiral, symmetrically spiraling about the main axis x.

According to some embodiments, as shown in FIG. 4, a tapered tip 421 of the first spout portion 420 may be directed along the main axis x.

According to some embodiments, as shown in FIG. 4, a tip 431 of the second spout portion 430 may be directed along the main axis x.

According to some embodiments, the overall width of the first spout portion d12 and/or the overall width of the second spout portion d13 may be significantly larger than the largest width of the tubular portion d10, to prevent the occluding element(s) from drifting inside the patient's ureter at least towards the kidney and optionally, also from drifting towards the bladder. This may be achieved by having the first and the second spout portions 420 and 430 protrude from the border contours of the tubular portion 410, such that at least the second spout portion 430 engages with the inner walls of the ureter and/or the occluding element(s), and the first spout portion 420 is either located in the patient's kidney, once deployed or engages the inner wall of the patient's ureter and/or the occluding element(s). For example, the overall width of the first and/or second spout portions d12 and/or d13, respectively, may be equal or substantially equal to an average diameter of a ureter inner wall.

According to some embodiments, the tip 421 of the first spout portion 420 and/or the tip 431 of the second spout portion 430 may be directed along the main axis x to prevent these tips 421/431 from engaging the inner walls tissue of the ureter, the kidney and/or the bladder during and/or after deployment of the ureteral stent 400.

FIG. 5 shows a flowchart of a process for using a ureteral stent with at least one tapered edge, according to some embodiments. The process may include providing a ureteral stent having a tubular portion, a first spout portion that has a curved shape in its relaxed state and has a tapered tip and a second spout portion that has a curved shape in its relaxed state having a tapered or non-tapered tip (block 510); and deploying the ureteral stent in a patient's body, such that the first spout portion thereof is located in the patient's kidney or in the ureter proximal to the kidney and the second spout portion thereof is located in the patient's bladder or in the ureter side that distal to the kidney, where the tubular portion of the ureteral stent is located over one or more occluding elements in the patient's ureter, such as to form a bridging channel for enabling fluid flow passed the one or more occluding elements (block 520).

FIG. 6 shows a flowchart of a process of deployment of a ureteral stent in a patient's body, according to some embodiments. The process may include threading a guide element such as a guide wire through the ureteral stent, thereby causing or to cause its spout portions to unfold from their relaxed state curved shape (block 610); guiding the guide element and the ureteral stent in which the guide element is threaded, to a desired location of the stent (e.g. at least partially in the ureter) such that first spout portion is located at one side of the occluding element(s) and the second spout portion is located at an opposite side of the occluding element(s), where the tubular portion forms a bridge over the occluding element(s) (block 620); and removing the guide element from the ureteral stent, once in place, to cause or thereby causing the spout portions to fold back into their relaxed curved shape (block 630).

According to some embodiments, the entire deployment of the ureteral stent may be carried out while using one or more imaging and/or sensing systems/devices, etc., configured to sense one or more parameters or images indicative of the location of at least part of the ureteral stent, during deployment thereof, in real time or near real time, e.g., to remove the guide element only when the ureteral stent is in its desired orientation and/or position relative to the patient's ureter.

Figure 7:
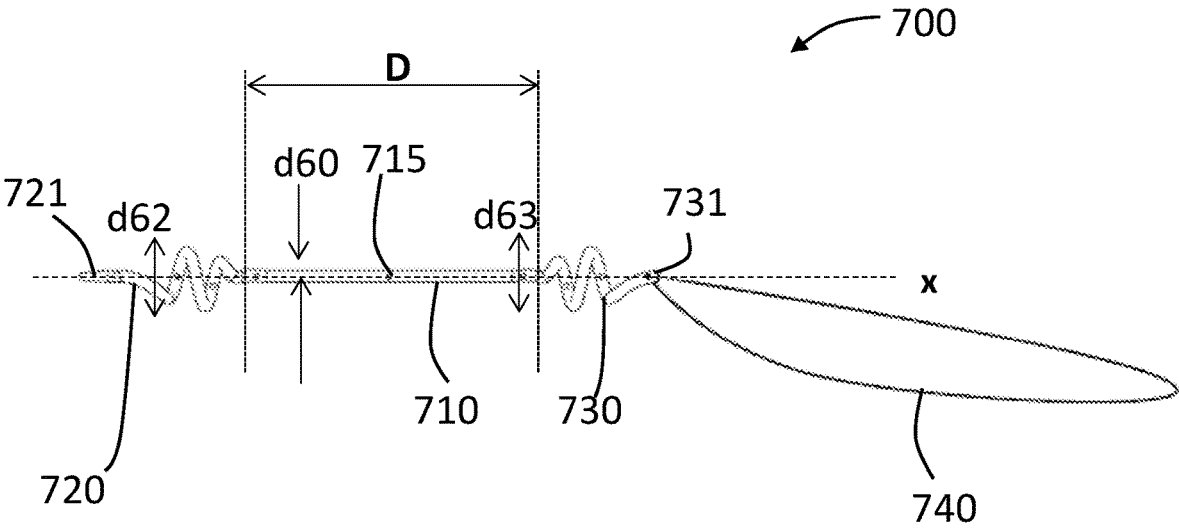
FIG. 7 shows a short ureteral stent, having an overall length that enables it to reside entirely within a patient's ureter once deployed therein, according to some embodiments.
Figure 8:
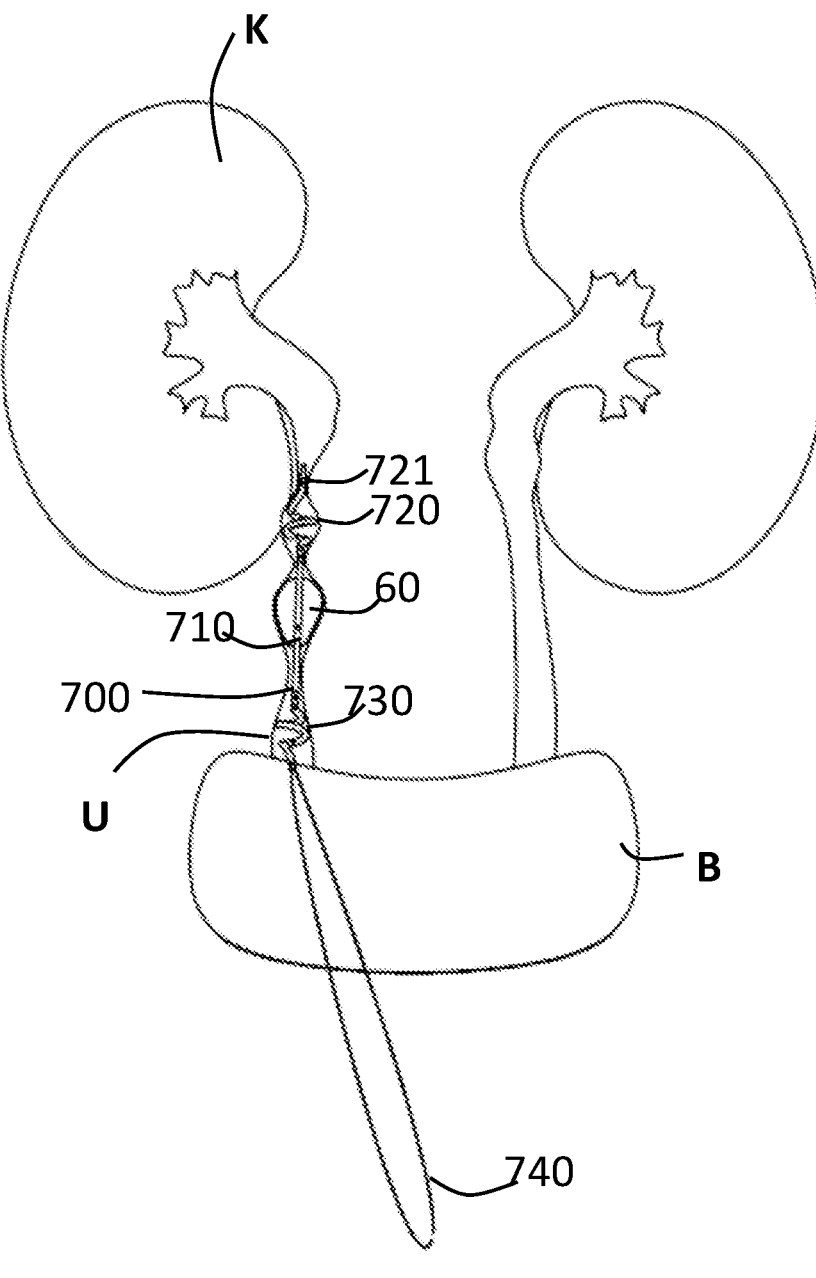
FIG. 8 shows the short ureteral stent deployed in a patient's ureter.

FIGS. 7 and 8 show a ureteral stent having an overall length (at least in a relaxed state thereof) that enables the ureteral stent, once deployed, to reside entirely in the patient's ureter, according to some embodiments.

According to these embodiments, a ureteral stent 700 is similar in design to ureteral stent 400, having an overall length that may be smaller than an average or personal length of a patient's ureter to be entirely located within the ureter once fully deployed.

The ureteral stent 700 includes a tubular (straight) portion 710 of length D and extending along a main axis x, a first spout portion 720, a second spout portion 730, and a string 740, connecting to the second spout portion 730. The first and second spout portions 720 and 730 extend from opposite sides of the tubular portion 710 and may, optionally, also be tubular.

According to some embodiments, the overall width of the first spout portion d62 and/or the overall width of the second spout portion d63 may be significantly larger than the largest width of the tubular portion d60, to prevent the occluding element(s) from drifting inside the patient's ureter at least towards the kidney and optionally, also from drifting towards the bladder. This may be achieved by having the first and the second spout portions 720 and 730 protrude from the border contours of the tubular portion 710, such that at least the first spout portion 720 engages with the inner walls of the ureter and/or with the occluding element(s).

According to some embodiments, a proximal tip 721 of the first spout portion 720 and/or a distal tip 731 of the second spout portion 730 may be directed inwardly towards or along the main axis x to prevent these ends or tips 721/731 from engaging the inner walls tissue of the ureter once deployed.

FIG. 8 shows the ureteral stent 700 deployed within a patient's ureter U connecting one kidney K of the patient to the bladder B. It is shown that the protruding first and second spout portions 720 and 730 form a bordering area enclosing the occluding element 60 therein, for preventing the occluding element 60 at least from reaching the patient's kidney K over time, while enabling fluid passage from the kidney K to the bladder B, by bypassing and bridging over the occluding element 60.

According to some embodiments, the tubular portion 710 of the ureteral stent 700 may also include one or more openings 715 for improving fluid flow through the ureteral stent 700.

Each one or more of: the tip 721 of the first spout portion 720 and/or the tip 731 of the second spout portion 730, may be tapered.

According to some embodiments, the length D of the tubular portion 710 of the ureteral stent 700, when in relaxed state, may be ranging, for example, between 5 cm and 15 cm, where 24 cm to 28 cm is an average length range for adult patient ureters.

FIG. 9 shows a flowchart of a process for using a ureteral stent configured for being entirely resided in a patient's ureter once deployed therein, according to some embodiments. The process may include providing a ureteral stent having a tubular portion, a first spout portion and a second spout portion, where the overall length of the ureteral stent is such that, once deployed, it resides entirely within the patient's ureter (block 910); and deploying the ureteral stent in a patient's body, such that it resides entirely within the patient's ureter and optionally borders the occluding element(s) in the ureter, at least from one side thereof that is proximal to the patient's kidney (block 912).

The deployment of the ureteral stent may be like the deployment process described in FIG. 6.

ADDITIONAL EXAMPLES

Example 1 is a ureteral stent comprising: a tubular portion having an elongated hollow tubular shape having a first edge and a second edge, the tubular portion being configured for enabling fluid flow therethrough; a first spout portion, which extends from the first edge of the tubular portion, the first spout portion being configurable to a curved shape, in a relaxed state of the ureteral stent; and a second spout portion, which extends from the second edge of the tubular portion, the second spout portion being configurable to a curved shape, in a relaxed state of the ureteral stent, wherein the ureteral stent is configured to be at least partially deployed in a patient's ureter such that the first spout portion is located at a smaller distance from a patient's kidney than the second spout portion, wherein the ureteral stent is configured to enable, when deployed in the patient's body, fluid passage between the kidney and the bladder of the patient, by bypassing one or more partially and/or fully occluded sections of a patient's ureter; and wherein the diameter of at least part of at least one of: the first spout portion and/or the second spout portion is smaller than the diameter of at least part of the tubular portion. A section of a ureter may be partially or fully blocked due to a stone, a stricture and/or the like.

In example 2, the subject matter of example 1 may include, wherein the overall length of the ureteral stent is such that once deployed in a patient's body, the first spout portion of the ureteral stent is in the patient's ureter or kidney and the second spout portion of the ureteral stent is located in the patient's ureter or bladder.

In example 3, the subject matter of examples 1 to 2 may include, wherein the tubular portion is porous.

In example 4, the subject matter of examples 1 to 2 may include, wherein the tubular portion comprises at least one opening.

In example 5, the subject matter of examples 1 to 4 may include, wherein the first spout portion and/or the second spout portion curved shape is such that its overall width is larger than the diameter and/or width of the tubular portion.

In example 6, the subject matter of example 5 may include, wherein the curved shape of the first spout portion and/or of the second spout portion comprises: a spiral shape, a pig tail shape, a conical spiral shape, and/or a tapering spiral shape.

In example 7, the subject matter of examples 1 to 6 may include, wherein: a tip of the first spout portion is configured to be directed inwardly, outwardly or in parallel to a main axis of the tubular portion; and/or a tip of the second spout portion is configured to be directed inwardly, outwardly or in parallel to a main axis of the tubular portion.

In example 8, the subject matter of examples 1 to 7 may include, wherein the tubular portion, the first spout portion and the second spout portion are all configured as a single integral stent piece.

In example 9, the subject matter of examples 1 to 7 may include, wherein the tubular portion is connectable to the first spout portion and to the second spout portion.

In example 10, the subject matter of examples 1 to 9 may include, wherein the first spout portion and/or the second spout portion is configured to be transitioned from its relaxed state tubular curved shape into a tensioned state when an elongated guide element is inserted through the ureteral stent; and wherein the first spout portion and/or the second spout portion are configured to transition to from the tensioned state into a tubular curved shape relaxed state when the elongated guide element is removed from the ureteral stent.

In example 11, the subject matter of examples 1 to 10 may include, wherein the tubular portion, the first spout portion, and/or the second spout portion comprises one or more shape memory materials.

In example 12, the subject matter of examples 1 to 11 may include, wherein the first spout portion, the second spout portion or one or both edges of the tubular portion are tapered, causing gradual narrowing of the diameter of the tubular portion towards one or more tips of the first spout portion and/or the second spout portion.

In example 13, the subject matter of examples 1 to 11 may include, wherein the tubular portion has an hourglass shape, for gradual narrowing and subsequent widening of the diameter of the tubular portion from the first edge towards the second edge of the tubular portion.

In example 14, the subject matter of examples 1 to 13 may include, wherein the ureteral stent further comprises a string connected to the second edge of the tubular portion or to the second spout portion.

In example 15, the subject matter of examples 1 to 14 may include, wherein: the widest diameter of the tubular portion ranges between 4.8 F and 8 F; the narrowest diameter of the first spout portion ranges between 3.6 F and 6 F; and the narrowest diameter of the second spout portion ranges between 3.6 F and 6 F.

In example 16, the subject matter of examples 1 to 15 may include, wherein the ratio between the widest diameter of the tube portion and the narrowest diameter of the first and/or second spout portions ranges between 1.33 and 2.22.

Example 17 is a method for prevention of ureter occlusion, the method comprising: (i) providing a ureteral stent comprising: a tubular portion having an elongated hollow tubular shape having a first edge and a second edge, the tubular portion being configured for enabling fluid flow therethrough; a first spout portion, which extends from the first edge of the tubular portion, the first spout portion being configurable to a curved shape in a relaxed state; and a second spout portion, which extends from the second edge of the tubular portion, the second spout portion being configurable to a curved shape in a relaxed state; and (ii) deploying the ureteral stent in a patient's body such that at least part thereof is located in the patient's ureter, wherein the ureteral stent is configured to enable, when deployed in a patient's body, fluid passage between the kidney and the bladder of the patient, by bypassing one or more partially and/or fully occluded ureter sections located in the patient's ureter, and wherein the diameter of at least part of at least one of: the first spout portion and/or the second spout portion is smaller than the diameter of at least part of the tubular portion.

In example 18, the subject matter of example 17 may include, wherein the deploying of the ureteral stent comprises: threading an elongated guide element through the ureteral stent, wherein the threading of the elongated guide element causes the first and second spout portions to unfold from their relaxed state curved shape; guiding the elongated guide element and the ureteral stent it is threaded through, to the ureter of a patient such that the first spout portion bypasses one or more partially or fully occluded sections of in the ureter, the tubular portion is positioned over one or more partially or fully occluding elements of the occluded sections and the second spout portion is located at a distal side of the one or more partially or fully occluding elements opposite the location of the proximal spout portion; and removing the elongated guiding element, once the ureteral stent is in the ureter, thereby causing the proximal and distal spout portions to attain the relaxed state, to enclose the one or more occluding elements.

In example 19, the subject matter of example 18 may include using one or more imaging systems for detecting the location of the ureteral stent throughout the deployment process.

Example 20 is a ureteral stent comprising: a tubular portion having an elongated hollow tubular shape having a first edge and a second edge, the tubular portion being configured for enabling fluid flow therethrough; a first spout portion, which extends from the first edge of the tubular portion, the first spout portion being configurable to a curved shape, in a relaxed state of the ureteral stent; and a second spout portion, which extends from the second edge of the tubular portion, the second spout portion being configurable to a curved shape, in a relaxed state of the ureteral stent, wherein the ureteral stent is configured to enable, when deployed in the patient's body, fluid passage between the kidney and the bladder of the patient, by bypassing one or more partially and/or fully occluded ureter sections, and wherein the overall length of the ureteral stent is such as to be completely located within a patient's ureter once deployed therein, such that both first and second spout portions of the ureteral stent are located within the patient's ureter.

In example 21, the subject matter of example 20 may include, wherein the first and/or the second spout portions border a one or more partially or fully occluding elements from at least one side of the one or more partially or fully occluding elements, when the stent is deployed in the patient's ureter.

In example 22, the subject matter of example 21 may include, wherein the ureteral stent is configured to border the one or more partially or fully occluding elements, by having its first and second spout portions engaged with the sides of the patient's ureter and/or engaged with the one or more occluding elements.

In example 23, the subject matter of examples 20 to 22 may include, wherein the tubular portion is porous.

In example 24, the subject matter of examples 20 to 23 may include, wherein the tubular portion comprises at least one opening.

In example 25, the subject matter of examples 20 to 24 may include, wherein: the first spout portion is at least partially spirally shaped defining a first spiral axis; and/or the second spout portion is at least partially spirally shaped defining a second spiral axis.

In example 26, the subject matter of examples 20 to 25 may include, wherein: a tip of the first spout portion is configured to be directed inwardly, outwardly or in parallel to a main axis of the tubular portion, when in a straight position; and/or a tip of the second spout portion is config- ured to be directed inwardly, outwardly or in parallel to a main axis of the tubular portion, when in a straight position.

In example 27, the subject matter of examples 20 to 26 may include, wherein the tubular portion, the first spout portion and the second spout portion are all configured as a single integral stent piece.

In example 28, the subject matter of examples 20 to 26 may include, wherein the tubular portion is made from a different material and/or of a different tube width than that of the first and/or second spout portions.

In example 29, the subject matter of examples 20 to 28 may include, wherein the first spout portion and/or the second spout portion is configured to be transitioned from its relaxed state tubular curved shape into a tensioned state when an elongated guide element is inserted through the ureteral stent; and wherein the first spout portion and/or the second spout portion are configured to transition to from the tensioned state into a tubular curved shape relaxed state when the elongated guide element is removed from the ureteral stent.

In example 30, the subject matter of examples 20 to 29 may include, wherein the tubular portion, the first spout portion, and/or the second spout portion comprises one or more shape memory materials.

In example 31, the subject matter of examples 20 to 30 may include, wherein the tubular portion defines a main axis in its relaxed state and wherein: the first spout portion is spirally curved defining a first spiral axis that is angular to the main axis; and/or the second spout portion is spirally curved defining a second spiral axis that is angular to the main axis.

In example 32, the subject matter of examples 20 to 31 may include, wherein the diameter of at least part of at least one of: the first spout portion and/or the second spout portion is smaller than the diameter of at least part of the tubular portion.

In example 33, the subject matter of examples 20 to 32 may include, wherein the ureteral stent further comprises a string connected to the second edge of the tubular portion or to the second spout portion.

In example 34, the subject matter of examples 20 to 32 may include, wherein the overall length of the ureteral stent in a relaxed state thereof, ranges between 5 cm and 26 cm.

Example 35 is a method for prevention of ureter occlu- sion, the method comprising: (i) providing a ureteral stent comprising: a tubular portion having an elongated hollow tubular shape having a first edge and a second edge, the tubular portion being configured for enabling fluid flow therethrough; a first spout portion, which extends from the first edge of the tubular portion, the first spout portion being configurable to a curved shape in a relaxed state; and a second spout portion, which extends from the second edge of the tubular portion, the second spout portion being configurable to a curved shape in a relaxed state; and (ii) deploying the ureteral stent in a patient's ureter, wherein the ureteral stent is configured to enable, when deployed in the patient's body, fluid passage between the kidney and the bladder of the patient, by bypassing one or more partially and/or fully occluded sections of a patient's ureter, and wherein the overall length of the ureteral stent is such as to be completely located within a patient's ureter once deployed therein, such that both first and second spout portions of the ureteral stent are located within the patient's ureter.

In example 36, the subject matter of example 35 may include, wherein the deploying of the ureteral stent com- prises: threading an elongated guide element through the ureteral stent, wherein the threading of the elongated guide element causes the first and second spout portions to unfold from their relaxed state curved shape; guiding the elongated guide element and the ureteral stent it is threaded through, to the ureter of a patient such that the first spout portion bypasses one or more partially or fully occluded sections in the ureter, the tubular portion is located over one or more partially or fully occluding elements and the second spout portion is located at an another side of the one or more partially or fully occluding elements opposite the location of the first spout portion; and removing the elongated guiding element, once the ureteral stent is in the ureter, thereby causing the first and second spout portions to attain the relaxed state, thereby enclosing the one or more occluding elements.

In example 37, the subject matter of example 36 may include, using one or more imaging systems for detecting the location of the ureteral stent throughout the deployment process.

While the invention has been described with respect to a limited number of embodiments, these should not be construed as limitations on the scope of the invention, but rather as exemplifications of some of the embodiments.

In the discussion, unless otherwise stated, adjectives such as "substantially" and "about" "approximately", that modify a condition or relationship characteristic of a feature or features of an embodiment of the invention, are to be understood to mean that the condition or characteristic is defined to within tolerances that are acceptable for operation of the embodiment for an application for which it is intended.

Unless otherwise specified, the terms "substantially", "'about" and/or "close" with respect to a magnitude or a numerical value may imply to be within an inclusive range of −10% to +10% of the respective magnitude or value.

It is important to note that the method may include is not limited to those diagrams or to the corresponding description. For example, the method may include additional or even fewer processes or operations in comparison to what is described in the figures. In addition, embodiments of the method are not necessarily limited to the chronological order as illustrated and described herein.

It should be noted that where an embodiment refers to a condition of "above/below a threshold" or a "limit", this should not be construed as excluding an embodiment referring to a condition of "equal or above a threshold/limit". Analogously, where an embodiment refers to a condition "below a threshold", this should not to be construed as excluding an embodiment referring to a condition "equal or below a threshold". It is clear that should a condition be interpreted as being fulfilled if the value of a given parameter is above a threshold, then the same condition is considered as not being fulfilled if the value of the given parameter is equal or below the given threshold. Conversely, should a condition be interpreted as being fulfilled if the value of a given parameter is equal or above a threshold, then the same condition is considered as not being fulfilled if the value of the given parameter is below (and only below) the given threshold.

It should be understood that where the claims or specification refer to "a" or "an" element and/or feature, such reference is not to be construed as there being only one of those elements. Hence, reference to "an element" or "at least one element" for instance may also encompass "one or more elements".

Terms used in the singular shall also include the plural, except where expressly otherwise stated or where the context otherwise requires.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Unless otherwise stated, the use of the expression "and/or" between the last two members of a list of options for selection indicates that a selection of one or more of the listed options is appropriate and may be made. Further, the use of the expression "and/or" may be used interchangeably with the expressions "at least one of the following", "any one of the following" or "one or more of the following", followed by a listing of the various options.

It is appreciated that certain features of the invention, which are, for clarity, described in the context of separate embodiments or example, may also be provided in combination in a single embodiment. Conversely, various features of the invention, which are, for brevity, described in the context of a single embodiment, example and/or option, may also be provided separately or in any suitable sub-combination or as suitable in any other described embodiment, example or option of the invention. Certain features described in the context of various embodiments, examples and/or optional implementation are not to be considered essential features of those embodiments, unless the embodiment, example and/or optional implementation is inoperative without those elements.

It is noted that the terms "in some embodiments", "according to some embodiments", "according to some embodiments of the invention", "for example", "e.g.,", "for instance" and "optionally" may herein be used interchangeably.

The number of elements shown in the Figures should by no means be construed as limiting and is for illustrative purposes only.

Throughout this application, various embodiments may be presented in and/or relate to a range format. It should be understood that the description in range format is merely for convenience and brevity and should not be construed as an inflexible limitation on the scope of the embodiments. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

What is claimed is:

1. A ureteral stent comprising:
   a tubular portion having an elongated hollow tubular shape having a first edge and a second edge, the tubular portion being configured for enabling fluid flow therethrough; a first spout portion, which extends from the first edge of the tubular portion, the first spout portion being configurable to a curved shape, in a relaxed state of the ureteral stent; and a second spout portion, which extends from the second edge of the tubular portion, the second spout portion being configurable to a curved shape, in a relaxed state of the ureteral stent,
   wherein the ureteral stent is configured to enable, when deployed in the patient's body, fluid passage between a kidney and the bladder of the patient, by bypassing one or more partially and/or fully occluded sections of a patient's ureter,
   wherein the overall length of the ureteral stent is such as to be completely located within a patient's ureter once deployed therein, such that both first and second spout portions of the ureteral stent are located within the patient's ureter; and wherein, when the stent is deployed in the patient's ureter, the first and the second spout portions engage with the proximal and distal sides of the one or more partially or fully occluding elements, respectively, such that the one or more partially or fully occluding elements is positioned between the first spout portion and the second spout portion.

2. The ureteral stent of claim 1, wherein the first and/or the second spout portions are configured to border the one or more partially or fully occluding elements from at least one side of one or more partially or fully occluding elements, when the stent is deployed in the patient's ureter.

3. The ureteral stent of claim 2, wherein the ureteral stent is configured to border the one or more partially or fully occluding elements, by having the first and second spout portions engaged with the sides of the patient's ureter and/or engaged with the one or more occluding elements.

4. The ureteral stent of claim 1, wherein the tubular portion is porous.

5. The ureteral stent of claim 1, wherein the tubular portion comprises at least one opening.

6. The ureteral stent of claim 1, wherein:
the first spout portion is at least partially spirally shaped defining a first spiral axis; and/or
the second spout portion is at least partially spirally shaped defining a second spiral axis.

7. The ureteral stent of claim 1, wherein:
a tip of the first spout portion is configured to be directed inwardly, outwardly or in parallel to a main axis of the tubular portion, when in a straight position; and/or
a tip of the second spout portion is configured to be directed inwardly, outwardly or in parallel to a main axis of the tubular portion, when in a straight position.

8. The ureteral stent of claim 1,
wherein the first spout portion and/or the second spout portion is configured to be transitioned from its relaxed state tubular curved shape into a tensioned state when an elongated guide element is inserted through the ureteral stent; and
wherein the first spout portion and/or the second spout portion are configured to transition to from the tensioned state into a tubular curved shape relaxed state when the elongated guide element is removed from the ureteral stent.

9. The ureteral stent of claim 1, wherein the tubular portion defines a main axis in its relaxed state and wherein:
the first spout portion is spirally curved defining a first spiral axis that is angular to the main axis; and/or
the second spout portion is spirally curved defining a second spiral axis that is angular to the main axis.

10. The ureteral stent of claim 1, wherein a diameter of at least part of at least one of: the first spout portion and/or the second spout portion is smaller than a diameter of at least part of the tubular portion.

11. The ureteral stent of claim 1, wherein an overall length of the ureteral stent in a relaxed state thereof, ranges between 5 cm and 28 cm.

12. A ureteral stent comprising:
a tubular portion having an elongated hollow tubular shape having a first edge and a second edge, the tubular portion being configured for enabling fluid flow therethrough; a first spout portion, which extends from the first edge of the tubular portion, the first spout portion being configurable to a curved shape, in a relaxed state of the ureteral stent; and a second spout portion, which extends from the second edge of the tubular portion, the second spout portion being configurable to a curved shape, in a relaxed state of the ureteral stent,
wherein the ureteral stent is configured to be at least partially deployed in a patient's ureter such that the first spout portion is located at a smaller distance from the patient's kidney than the second spout portion,
wherein the ureteral stent is configured to enable, when deployed in the patient's body, fluid passage between the kidney and the bladder of the patient, by bypassing one or more partially and/or fully occluding elements located in the patient's ureter;
wherein, when the stent is deployed in the patient's ureter, the first and the second spout portions engage with the proximal and distal sides of the one or more partially or fully occluding elements, respectively;
wherein a first diameter of at least part of at least one of: the first spout portion and/or the second spout portion is smaller than a second diameter of at least part of the tubular portion; and
wherein, when the stent is deployed in the patient's ureter, the first and the second spout portions engage with the proximal and distal sides of the one or more partially or fully occluding elements, respectively, such that the one or more partially or fully occluding elements is positioned between the first spout portion and the second spout portion.

13. The ureteral stent of claim 12, wherein the overall length of the ureteral stent is such that once deployed in a patient's body, the first spout portion of the ureteral stent is positioned in the patient's ureter or kidney and the second spout portion of the ureteral stent is located in the patient's ureter or bladder.

14. The ureteral stent of claim 12, wherein the tubular portion comprises at least one opening.

15. The ureteral stent of claim 12, wherein the first spout portion and/or the second spout portion curved shape is such that its overall width is larger than the diameter and/or width of the tubular portion.

16. The ureteral stent of claim 15, wherein the curved shape of the first spout portion and/or of the second spout portion comprises: a spiral shape, a pig tail shape, a conical spiral shape, and/or a tapering spiral shape.

17. The ureteral stent of claim 12, wherein: a tip of the first spout portion is configured to be directed inwardly, outwardly or in parallel to a main axis of the tubular portion; and/or
a tip of the second spout portion is configured to be directed inwardly, outwardly or in parallel to a main axis of the tubular portion.

18. The ureteral stent of claim 12, wherein the first spout portion, the second spout portion or one or both edges of the tubular portion are tapered, causing gradual narrowing of the diameter of the tubular portion towards one or more tips of the first spout portion and/or the second spout portion.

19. The ureteral stent of claim 12, wherein the tubular portion has an hourglass shape, for gradual narrowing and subsequent widening of the diameter of the tubular portion from the first edge towards the second edge of the tubular portion.

20. A method for prevention of ureter occlusion, the method comprising:

providing a ureteral stent comprising:

a tubular portion having an elongated hollow tubular shape having a first edge and a second edge, the tubular portion being configured for enabling fluid flow therethrough;

a first spout portion, which extends from the first edge of the tubular portion, the first spout portion being configurable to a curved shape in a relaxed state; and a second spout portion, which extends from the second edge of the tubular portion, the second spout portion being configurable to a curved shape in a relaxed state; and deploying the ureteral stent in a patient's body such that at least part thereof is positioned in the patient's ureter, wherein the ureteral stent is configured to enable, when deployed in a patient's body, fluid passage between the kidney and the bladder of the patient, by bypassing one or more partially and/or fully occluding elements located in the patient's ureter;

wherein, when the stent is deployed in the patient's ureter, the first and the second spout portions engage with the proximal and distal sides of the one or more partially or fully occluding elements, respectively;

wherein a first diameter of at least part of at least one of: the first spout portion and/or the second spout portion is smaller than a second diameter of at least part of the tubular portion; and wherein, when the stent is deployed in the patient's ureter, the first and the second spout portions engage with the proximal and distal sides of the one or more partially or fully occluding elements, respectively, such that the one or more partially or fully occluding elements is positioned between the first spout portion and the second spout portion.

\* \* \* \* \*